United States Patent
Straaijer (10) Patent No.: US 8,792,096 B2
(45) Date of Patent: Jul. 29, 2014

(54) INSPECTION APPARATUS FOR LITHOGRAPHY

(75) Inventor: Alexander Straaijer, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 669 days.

(21) Appl. No.: 12/922,587

(22) PCT Filed: Mar. 24, 2009

(86) PCT No.: PCT/EP2009/002136
§ 371 (c)(1),
(2), (4) Date: Dec. 9, 2010

(87) PCT Pub. No.: WO2009/118148
PCT Pub. Date: Oct. 1, 2009

(65) Prior Publication Data
US 2011/0102793 A1    May 5, 2011

Related U.S. Application Data

(60) Provisional application No. 61/064,728, filed on Mar. 24, 2008.

(51) Int. Cl.
*G01J 4/00*    (2006.01)
(52) U.S. Cl.
USPC ............................ 356/369; 356/492; 356/496
(58) Field of Classification Search
CPC ................ G01N 21/211; G01N 21/21; G01N 2021/213; G01J 4/00; G01B 11/0641
USPC .......................................... 356/369, 492, 496
See application file for complete search history.

(56) References Cited

U.S. PATENT DOCUMENTS

| | | | | |
|---|---|---|---|---|
| 5,311,285 A | * | 5/1994 | Oshige et al. | 356/369 |
| 5,335,066 A | * | 8/1994 | Yamada et al. | 356/364 |

(Continued)

FOREIGN PATENT DOCUMENTS

| | | |
|---|---|---|
| EP | 1 400 860 A2 | 3/2004 |
| EP | 1 628 164 A2 | 2/2006 |

OTHER PUBLICATIONS

International Preliminary Report on Patentability with Written Opinion of the International Searching Authority directed to related International Application No. PCT/EP2009/056431, mailed on Dec. 16, 2010, The International Bureau of WIPO, Geneva, Switzerland; 8 pages.

(Continued)

*Primary Examiner* — Tarifur Chowdhury
*Assistant Examiner* — Isiaka Akanbi
(74) *Attorney, Agent, or Firm* — Sterne, Kessler, Goldstein & Fox P.L.L.C.

(57) ABSTRACT

Four separately polarized beams are simultaneously measured upon diffraction from a substrate (W) to determine properties of the substrate. Linearly, circularly or elliptically polarized radiation is transmitted through a first beam splitter (N-PBS) and split into two polarized beams. These two beams are further split into two further beams using two further beam splitters, the further beam splitters (32,34) being rotated by 45° with respect to each other. The plurality of polarizing beam splitters enables the measurement of the intensity of all four beams and thus the measurement of the phase modulation and amplitude of the combined beams to give the features of the substrate. Algorithms are used to compare the four intensities of each of the polarized angles to give rise to the phase difference between the polarization directions and the ratio between the two main polarization direction amplitudes of the original polarized beam.

23 Claims, 5 Drawing Sheets

(56) References Cited

U.S. PATENT DOCUMENTS

| | | | |
|---|---|---|---|
| 5,880,838 A | 3/1999 | Marx et al. | |
| 6,211,955 B1* | 4/2001 | Basiji et al. | 356/326 |
| 6,384,916 B1* | 5/2002 | Furtak | 356/369 |
| 7,230,703 B2 | 6/2007 | Sezginer et al. | |
| 2001/0021018 A1* | 9/2001 | Basiji et al. | 356/326 |
| 2002/0106821 A1 | 8/2002 | Bode et al. | |
| 2002/0146734 A1* | 10/2002 | Ortyn et al. | 435/6 |
| 2003/0174340 A1* | 9/2003 | Hill | 356/496 |
| 2008/0198380 A1 | 8/2008 | Straaijer et al. | |
| 2009/0002706 A1 | 1/2009 | Weiss et al. | |

OTHER PUBLICATIONS

International Search Report mailed Jun. 16, 2009 for International Application No. PCT/EP2009/002136, 5 pgs.

Compain E, et al., "Complete Mueller Matrix Measurement with a Single High Frequency Modulation," Thin Solid Films, Elsevier-Sequoia S.A. Lausanne, CH, vol. 313-314, Feb. 13, 1998, pp. 47-52.

* cited by examiner

INSPECTION APPARATUS FOR LITHOGRAPHY

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Although scatterometry is a relatively quick form of analysis of a surface, measuring only the intensity of scattered radiation is not the most precise of measurements, as it does not take into account the different behavior of radiation that is polarized in different directions. For example, if the substrate object that is being measured is in the form of a grating that is aligned with one polarization direction, radiation polarized in that direction will scatter in a very different manner from radiation polarized in the orthogonal direction. To take polarization directions into account, an ellipsometric system has been envisaged that enables certain parameters of orthogonally polarized beams to be measured.

The prior art describes an ellipsometric system that enables certain parameters of orthogonally polarized beams to be measured. In one example of a known system, illumination radiation from a source is reflected from a structure on a target portion of a substrate and on its return journey from the substrate, it is linearly polarized along one of the two eigenpolarizations of three beam splitters that are present in the sensor. A first beam splitter sends part of the illumination to an imaging branch; a second beam splitter sends part of the illumination to a focus branch and a third beam splitter is a non-polarizing beam splitter that directs part of the beam to a camera CCD. Having passed through the non-polarizing beam splitter, the polarized beam passes through a phase modulator where its ordinary and extraordinary axis have been positioned at 45° with respect to the x and y directions. Subsequently, the beam is divided into its respective x- and y-polarization orientations using a Wollaston prism and impinges on a camera CCD. The relative intensities of the polarized beams are used to determine the relative polarization orientations of the different parts of the beam. From the relative polarization orientations, the effect of the structure on the beam can be determined. From the effect the structure has on the beam, the properties of the structure itself can be determined. The phase modulator is dependent on the wavelength of the radiation beam and has to be recalibrated for different types of radiation. Furthermore, the phase modulator system works only where both s- and p-polarization directions are available in the radiation to be measured. Once elliptically polarized radiation reflects from a substrate surface, depending on the azimuthal angle, either only the p-polarized radiation will be successfully reflected, only the s-polarized radiation, or a combination of the two. The combination is at a 50:50 ratio only on azimuthal angles of 45° and 135° if the polarization directions are 0° and 90°, for instance. Because of this, the information available from other azimuthal angles of the incident radiation beam is not available or at least very limited.

U.S. Pat. No. 5,880,838 (Marx et al.) also describes the measurement of a structure on a substrate using ellipsometry, wherein the measurement system is called polarization quadrature measurement (PQM). This document describes focusing a polarized beam of light (with TE and TM fields) onto the structure. The TM and TE fields are affected differently by the diffraction off the structure. The TE field can be used as a reference to analyze the phase and amplitude changes in the TM field. The relationship between phases and amplitudes of the TE and TM fields is dependent on the structural parameters (e.g. the depth of a hole or the height of a grating bar or the pitch of a grating) of the structure. By measuring this relationship, therefore, the structural parameters may be determined. Again, however, information relating to azimuthal angle of the incident radiation beam is not available.

SUMMARY

It is desirable to provide an ellipsometric function in a scatterometer such that phase difference between polarization directions and the ratio between polarization direction amplitudes of a radiation beam diffracted from a structure may be measured for a full range of azimuthal angles.

According to an aspect of the invention, there is provided an inspection apparatus, a lithographic apparatus and a lithographic cell configured to measure a property of a substrate, the inspection apparatus, lithographic apparatus and lithographic cell including: a radiation source configured to supply a radiation beam; an optical element configured to focus the radiation beam onto a substrate; a beam splitter system configured to split the radiation beam once reflected from the substrate into at least four components, each with a different polarization orientation; a detector configured to detect simultaneously angle-resolved spectra of the four components of the radiation beam; and a processor configured to use the angle-resolved spectra of the four components to determine a phase difference ($\Delta$) and a ratio (tan $\Psi$) between the polarization orientation amplitudes of the reflected radiation beam.

According to another aspect of the present invention, there is provided a method of measuring a property of a substrate, the method including: providing a radiation beam with elliptical polarization; reflecting the radiation beam off the surface of a substrate; splitting the reflected radiation beam into first and second orthogonally polarized sub-beams; splitting the first sub-beam into first and second components with polarization orientations of about 0 and 90 degrees respectively; splitting the second sub-beam into third and fourth components with polarization orientations of about 45 and 135 degrees respectively; simultaneously detecting all four components; and using the angle-resolved spectra of the four polarization orientations to determine a phase difference ($\Delta$) and a ratio (tan $\Psi$) between polarization orientation amplitudes of the reflected radiation beam.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
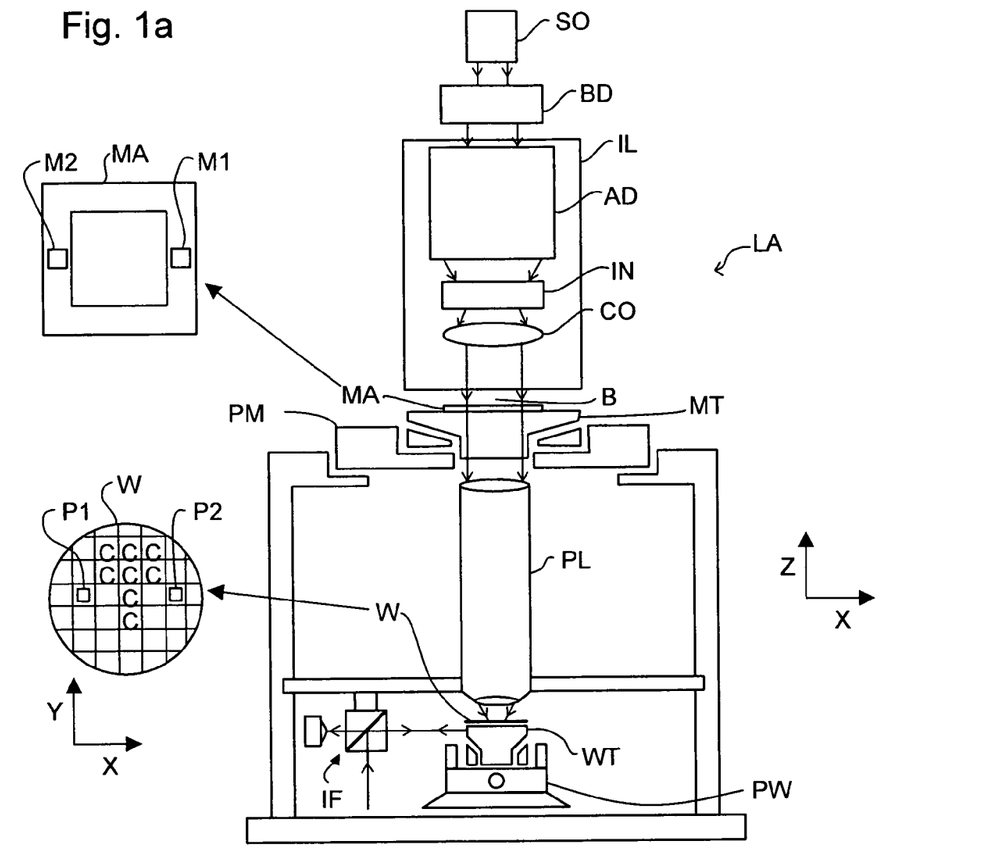
FIG. 1a depicts a lithographic apparatus according to an embodiment of the invention.

FIG. 1a schematically depicts a lithographic apparatus. The apparatus includes an illumination system (illuminator) IL configured to condition a radiation beam B (e.g. UV radiation or EUV radiation); a patterning device support or support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the patterning device support (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the patterning device (e.g. mask) MA with respect to the path of the radiation beam B, e.g. after mechanical retrieval from a mask library, or during a scan. In general, movement of the patterning device support (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the patterning device support (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device support (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
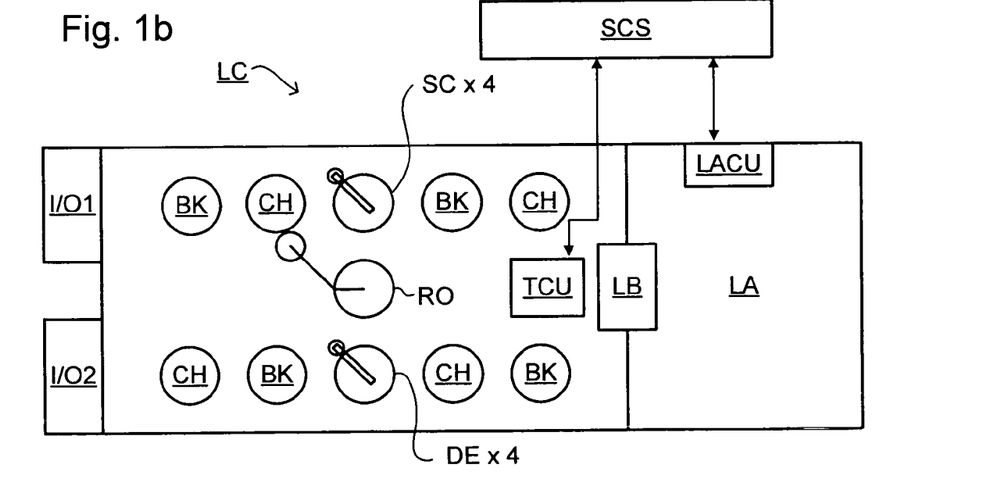
FIG. 1b depicts a lithographic cell or cluster according to an embodiment of the invention.

As shown in FIG. 1b, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 2:
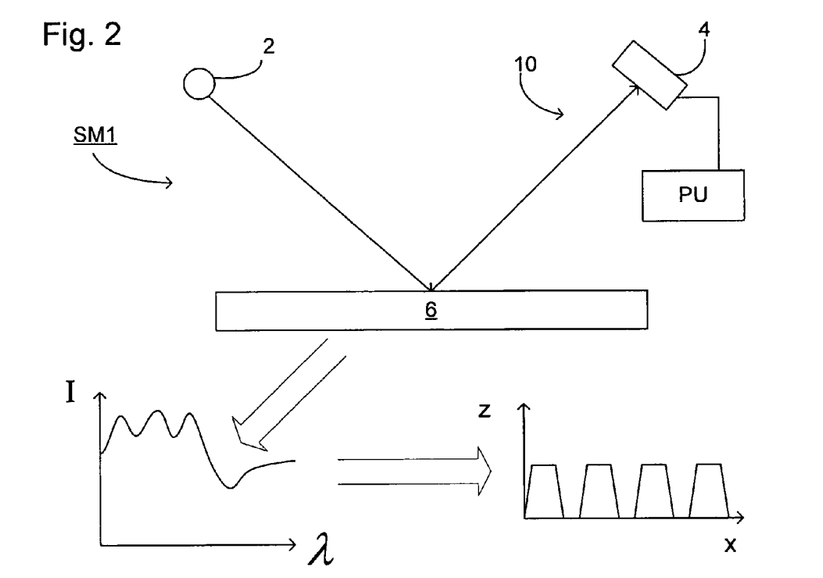
FIG. 2 depicts a scatterometer according to an embodiment of the invention.

FIG. 2 depicts a scatterometer SM1 which may be used in an embodiment of the present invention. It includes a broadband (white light) radiation projector 2 which projects radiation onto a target 6 of a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis (or other mathematical reconstruction models) and non-linear regression or by comparison with a library of simulated spectra as shown at the bottom of FIG. 2. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 3:
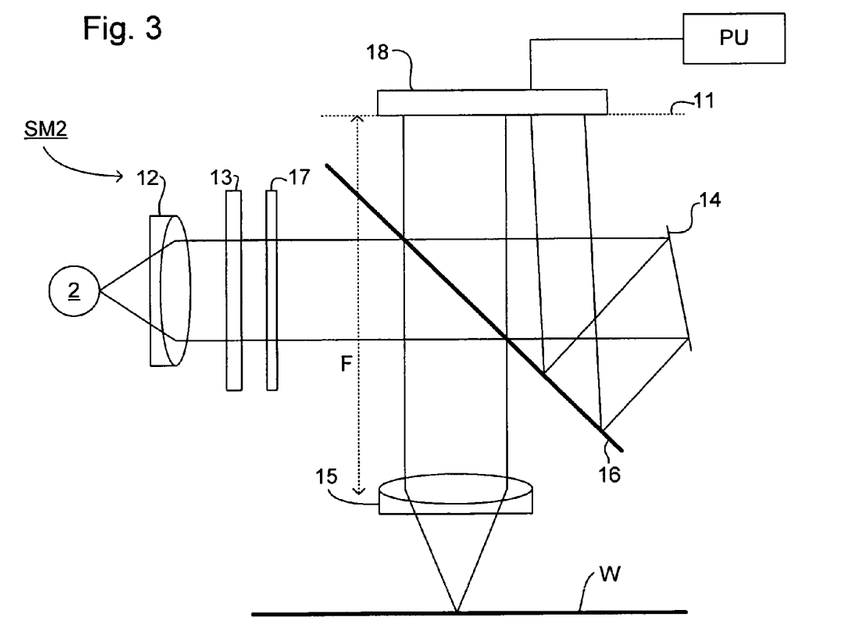
FIG. 3 depicts a scatterometer according to an embodiment of the invention.

Another scatterometer SM2 that may be used in an embodiment of the present invention is shown in FIG. 3. In this device, the radiation emitted by radiation source 2 is focused using lens system 12 through interference filter 13 and polarizer 17 to linearly polarize the radiation (or polarizer-retarder to create circularly polarized radiation, though there are many types of polarization that would work), reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuthal angle of the radiation. The detector is preferably a two-dimensional detector so that a two-dimensional angular scatter spectrum of the substrate target can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of about, say, 405-790 nm or even lower, such as 200-300 nm. The interference filter may be tunable rather than including a set of different filters. A grating could be used instead of interference filters.

The detector 18 may measure the intensity of scattered radiation at a single wavelength (or narrow wavelength range), the intensity separately at multiple wavelengths or integrated over a wavelength range. Furthermore, the detector may separately measure the intensity of transverse magnetic- and transverse electric-polarized radiation or light and/or the phase difference between the transverse magnetic- and transverse electric-polarized radiation or light.

Using a broadband radiation source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least $2\delta\lambda$ (i.e. twice the wavelength). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

As discussed above, a development from a simple scatterometer is an ellipsometer, which may be used to determine the shapes and other properties of structures on a substrate using slightly different parameters of the reflected light. The way this is done is shown in FIG. 4, which shows an ellipsometer according to an embodiment of the present invention.

Figure 4:
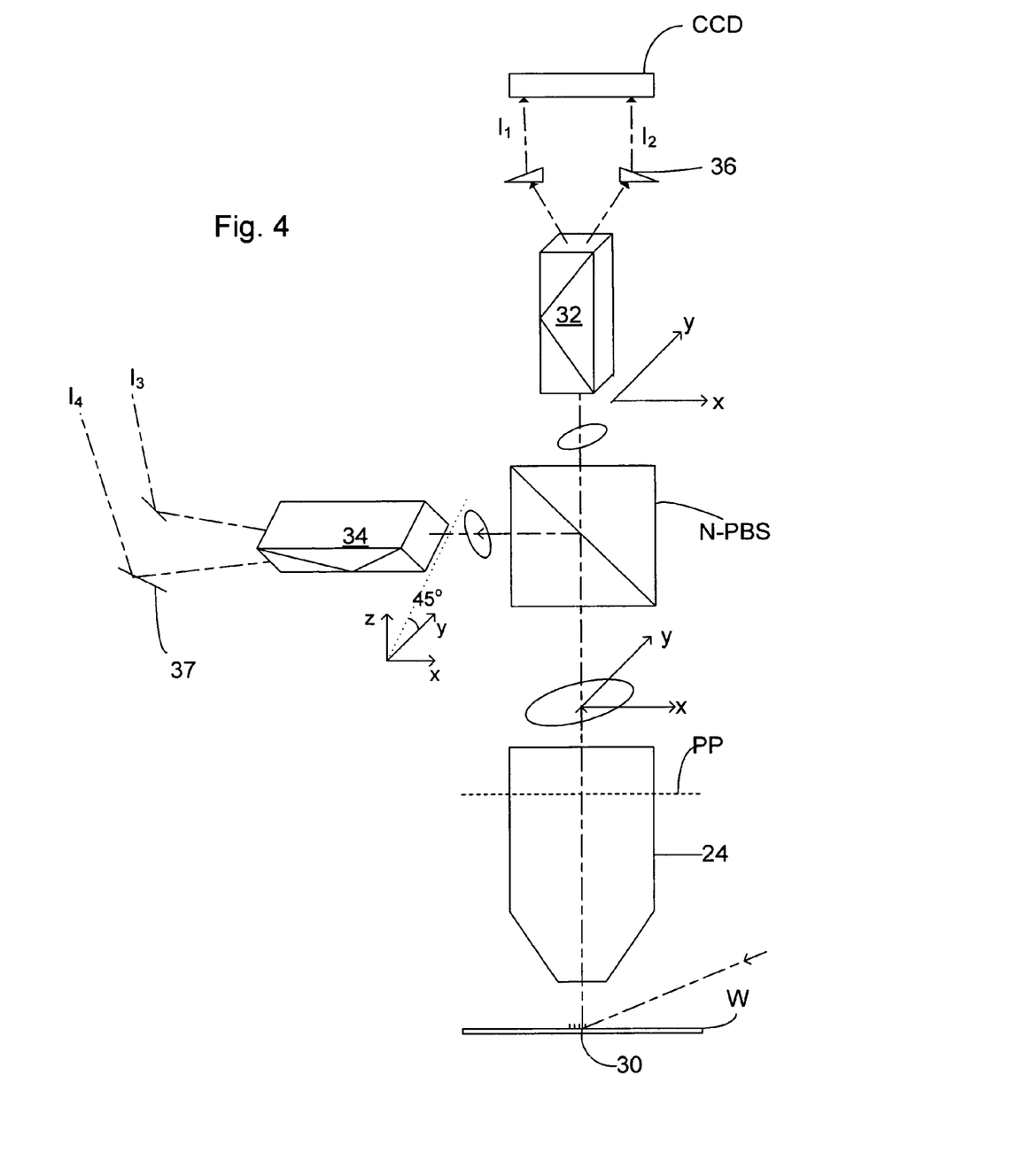
FIG. 4 depicts an ellipsometer according to an embodiment of the present invention.

FIG. 4 shows an example of an ellipsometric sensor (or an ellipsometer) such as that shown in FIG. 2 or 3, but that seeks to measure not only the reflectances of differently-polarized radiation, but also the phase difference ($\Delta$) and the ratio ($\Psi$) between differently-polarized radiation beam amplitudes. In the system shown in FIG. 4, elliptically polarized illumination radiation from source P is reflected from a structure 30 on a target portion of a substrate W and is focused through a microscope objective 24 onto the optics that will separate the polarization directions. The structure 30 may simply be a flat surface (e.g. with an oxide layer) for calibration purposes. The illumination radiation is elliptically polarized as shown by the ellipses in FIG. 4. The line across the microscope objective labeled PP is the pupil plane, which is the position at which the reflected radiation is focused. This focused image is refocused on to the surface of the camera CCD using standard optics. The reflected elliptically polarized radiation beam passes through a non-polarizing beam splitter N-PBS, where the beam is split into two elliptically polarized radiation beams. The first sub-beam continues into a polarizing beam splitter, such as Wollaston prism 32, that divides the elliptically polarized into its component linearly polarized components. The linearly polarized radiation beam components $I_1$ and $I_2$ are then focused on to the camera CCD, for example using optical wedges 36. The polarizing beam splitter 32 is aligned with the x and y axes of the radiation beam such that the elliptically polarized beam is divided into beams orthogonally polarized at 0° and 90°.

The other sub-beam that was split off from the main reflected beam at the non-polarizing beam N-PBS is directed into a second polarizing beam splitter 34. The elliptically polarized sub-beam in this branch is polarized in the same way as the first sub-beam. In order to obtain different polarization directions for components $I_3$ and $I_4$, the polarizing beam splitter 34 is rotated such that its axes are oriented at 45° to the y and z axes (the y and z axes defining a plane perpendicular to the x-y plane) as shown in FIG. 4. This polarizing beam splitter then divides the beam into components $I_3$ and $I_4$ to be detected on either the same or a different camera CCD as the first and second components $I_1$ and $I_2$. It will be understood that the direction of these third and fourth components (as with the first and second components) may be carried out using optical wedges 36 or deflectors 37. Alternatively, the camera may position such that wedges or deflectors are not required at all.

The relative intensities of the four polarized beam components ($I_1$, $I_2$, $I_3$, $I_4$) are used to determine the relative polarization orientations of the different parts of the beam. From the relative polarization orientations, the effect of the structure 30 on the beam as a whole can be determined because different reflecting edges of structures will affect the differently polarized states of the radiation in different ways.

From the effect the structure 30 has on the beam, the properties of the structure itself can be determined. The beam is reflected off the structure from several incident angles and from as many azimuthal angles as possible. A resulting intensity image looks like the images in FIG. 9, 10, 11 or 12. The specific images shown in these figures will be discussed later.

In the intensity images, smaller angles of incidence give rise to pixel values toward the middle of the image, such that a beam incident along the normal and reflecting along the normal gives rise to the pixel value in the middle of the circular image. The pixel values in a circumferential direction are linked to the azimuthal angle of the incident radiation beam.

If an incident beam is polarized such that it is s-polarized in one direction and p-polarized in the orthogonal direction, the two polarization directions will react differently to being reflected from a surface. Even if the surface is flat, if the azimuthal angle is such that the reflecting surface is aligned with one of the polarization directions, that polarization direction will survive intact, while the orthogonal polarization direction will be annihilated. In this way, there are two orthogonal directions (or azimuthal angles) from which only one polarization state will survive and only the information from that polarization state will be available for manipulation to determine the properties of the surface or structure from which the beam was reflected. At 45° to these orthogonal directions, equal amounts of the two orthogonally polarized portions of radiation beam will survive to the detector and form part of the image. Where phase modulators have been used in the prior art, because the applied phase shift between the two orthogonally polarized states needed to be known, both the s- and p-polarized states needed to be measurable and so only the 45° azimuthal angles provided the required information.

In an embodiment of the present invention, the two polarizing beam splitters 32 and 34 effectively act as phase shifters with respect to each other, changing the relative phases of the four linearly polarized beam components. From the known applied phase shift, the original phase difference ($\Delta$) may be determined. In other words, the radiation beam, in being divided into its respective polarization directions, effectively undergoes a relative phase shift and the detector CCD detects the intensities ($I_1$, $I_2$, $I_3$, $I_4$) of the four components with different polarization directions. These intensities ($I_1$, $I_2$, $I_3$, $I_4$) are then used to determine the properties of the reflected beam, and specifically the phase difference ($\Delta$) between the two linearly polarized beams that make up the elliptically polarized beams shown in FIG. 4, and the ratio (tan $\Psi$) between the amplitudes of these two linearly polarized beams that makes the overall radiation beam elliptically polarized. The phase difference is demonstrated in FIGS. 6 and 7.

Figure 6:
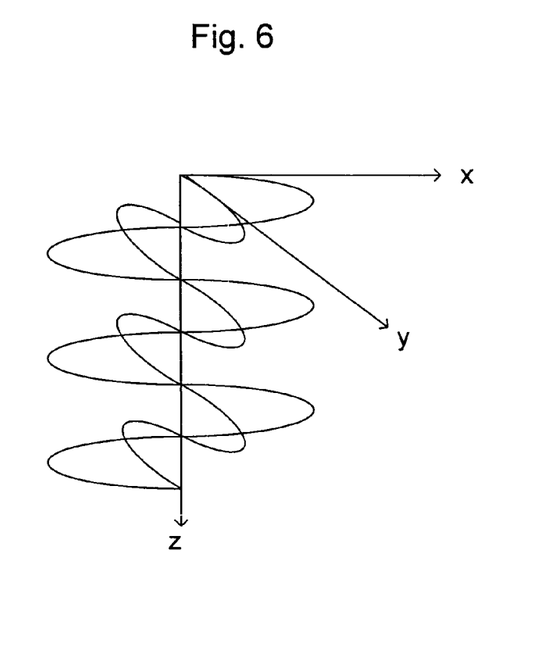
FIG. 6 depicts an elliptically polarized radiation beam.
Figure 7:
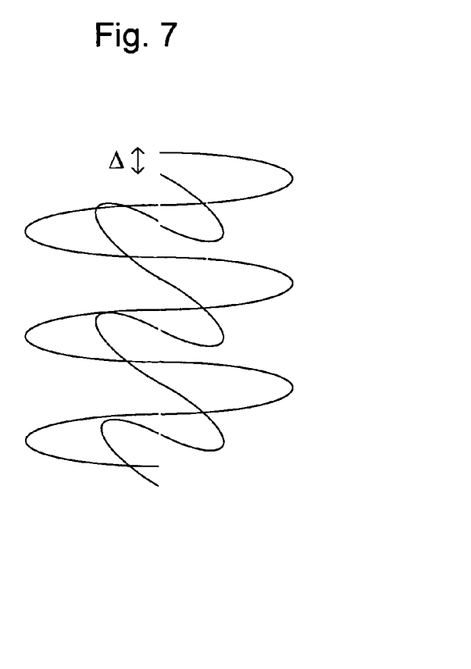
FIG. 7 depicts the relationship between reflected polarization directions with a phase shift between them.

Some background on radiation behavior will now be discussed. FIGS. 6 and 7 illustrate elliptically polarized beams. FIG. 6 illustrates a first polarization direction extending in an x direction and a second polarization direction extending in a y direction. The two polarization directions are in phase, which means that they have peaks and troughs in their wave amplitudes at the same points in a z direction. The ratio between the two polarization amplitudes is tan $\Psi$. If the amplitudes of each polarization direction are different, the result is an elliptically polarized beam. In FIG. 7, the angle between the two polarization directions is still 90°, but a phase shift has been applied. The phase shift is the effective time lag between the two polarization direction waves and is labeled as $\Delta$.

Generally, ellipsometry is the measurement of the state of polarization of scattered light. Ellipsometry measures two parameters: the phase difference ($\Delta$) between two differently polarized beams and an amplitude ratio (tan $\Psi$) of two polarized beams. With these two parameters, any polarization state of a purely polarized beam may be described.

Specifically, if an incident beam has both s and p polarizations, the reflected beam will have reflectance coefficients $R_p$ and $R_s$. The complex amplitudes of each polarization direction are represented by $E_p$ and $E_s$ and are calculated as $R_p*E_{p\text{-}in}$ and $R_s*E_{s\text{-}in}$, respectively (though the Imaginary parts of the complex amplitude being ignorable when only the intensities of the reflected beams are considered).

$\Delta$ (Delta) is the phase difference between the complex amplitudes $E_p$ and $E_s$ as given in equation (1) below.

The intensity of the received beam is proportional to the sum of the amplitudes, taking into account the angle of their relative polarization. This is why the amplitude ratio tan $\Psi$ is related to the angle $\Psi$ of the relative polarization of the beam.

If the polarizations of both $E_p$ and $E_s$ are aligned in the same orientation, the intensity of the received beam is at a maximum. If the two amplitudes are in orthogonal orientations, they cancel each other out and the intensity is at a minimum. The angle between the two polarization directions (or orientations) is $\Psi$ and so the relationship between $\psi$ and $E_p$ and $E_s$ is as follows in equation (2).

$$\Delta = \arg(E_p - E_s) \tag{1}$$

$$\tan \Psi = E_p/E_s \tag{2}$$

where $$E_p = R_p * E_{p\text{-}in} \tag{3}$$

$$E_s = R_s * E_{s\text{-}in} \tag{4}$$

The elliptically polarized beam can be basically reconstructed by a set of four measured intensities as shown in FIG. 6. If the overall intensity, I is given with the following formula:

$$I = 1 + a\cos(2A) + b\sin(2A) \tag{5}$$

wherein the Fourier coefficient are:

$$a = \left(\frac{I_1 - I_2}{I_1 + I_2}\right) \tag{6}$$

and $$b = \left(\frac{I_3 - I_4}{I_3 + I_4}\right), \tag{7}$$

and A is the azimuthal angle, the elliptically polarized beam is reconstructed for known values of $I_1$, $I_2$, $I_3$ and $I_4$.

Figure 5:
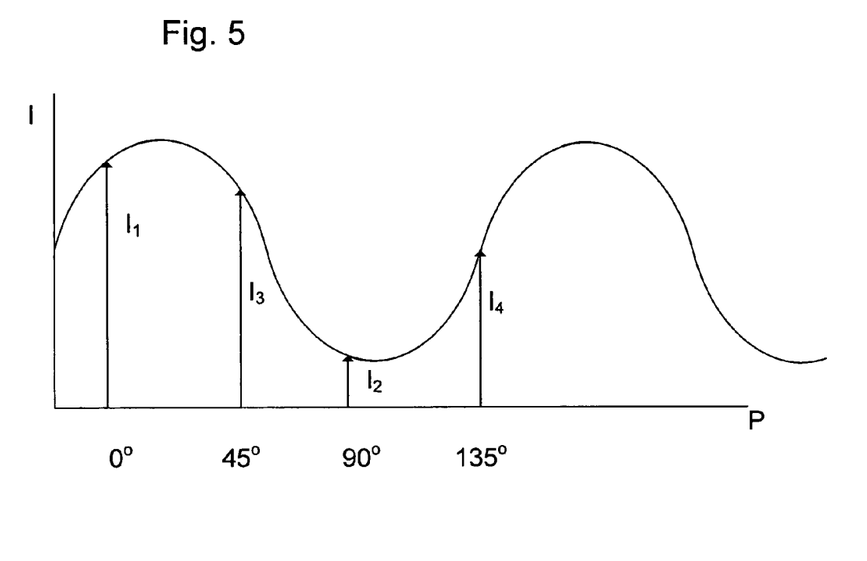
FIG. 5 depicts the relationship between intensity and polarization of a plurality of polarized beams according to an embodiment of the present invention.

Applying the relationship of the intensity of the elliptically polarized beam with the amplitude of the individual components (as shown in FIG. 5) gives the amplitudes that can be input into equations (1) and (2) above. The reconstructed beam thereby gives the phase difference ($\Delta$) and relative amplitude alignment ($\tan \Psi$), thus giving rise to the parameters of the structure 30.

The limitation with the method given above is that this only works in an ellipsometer when both the p- and s-polarizations are present. As discussed above, the only time both p- and s-polarizations are present is when the azimuthal angle of the radiation beam is such that both the p- and s-polarization directions are equally reflected. This generally occurs at azimuthal angles of 45° and 135°, where the s- and p-polarization directions are orthogonally 0° and 90° directions. The results above for $\Psi$ and $\Delta$ are therefore only available on the diagonals of the resulting intensity image detected and produced by the CCD detector, the diagonals being associated with the 45° and 135° azimuthal angles. A huge amount of information associated with the other angles is therefore not available. An embodiment of the present invention therefore seeks to be able to apply the above technique to every azimuthal angle in order to enable the use of all intensity measurements made by the CCD detector.

Figure 8:
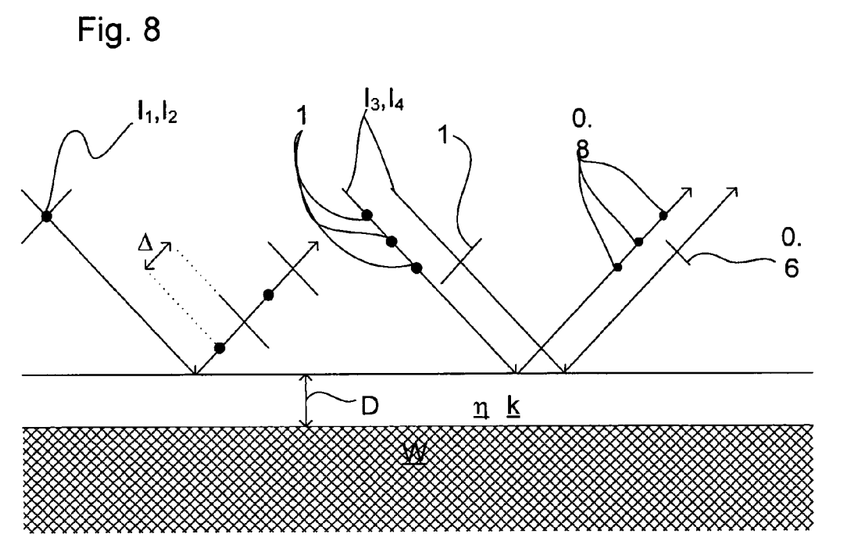
FIG. 8 depicts the behavior of polarized radiation reflecting from a surface.

FIG. 8 shows the four separate polarization directions (here labeled as $I_1$, $I_2$, $I_3$, and $I_4$) and how they reflect off the substrate W surface. The left-hand beam contains two components that are orthogonally polarized with respect to each other. The two polarization directions are depicted using a line for the polarization in the plane of the page and a black circle for perpendicular polarization into the page. As can be seen from FIG. 8, when the beam thus polarized is reflected from the surface of the substrate W a phase shift $\Delta$ is induced between the two components. The reflected beam with the phase shift is separated into its constituent components and detected. The phase shift caused by the reflection can be determined, giving rise to the property of the substrate at the point of reflection.

The right-hand beam of FIG. 8 shows the two components that are at 45° to the left-hand beam. Again, a line shows a first polarization direction and the black circle shows the orthogonal polarization direction. Giving the incoming beam an arbitrary value of 1 (1 being the full amount of the incident beam), the reflectance coefficient $R_S$ of the component with the polarization direction that is shown by the black circles is 0.8. In other words, 80% of the radiation polarized in this direction is reflected and detected. The reflectance coefficient $R_P$ for the component with the polarization direction shown as a line is given as 0.6 in this example. Using equation (2) above, $$\frac{R_P}{R_S} = \frac{0.6}{0.8} = 0.71$$

$$\Psi = \arctan(0.71) = 32°$$

From the knowledge of the phase difference $\Delta$ and the angle between the polarization direction $\Psi$, the thickness D of a resist layer on the substrate W, as well as the refractive index N and the absorption index k of the resist may be found using known methods.

The way that $\Delta$ and $\Psi$ are determined mathematically from the intensities of the four polarization directions will now be described.

From the CCD cameras, the intensity values $I_1$, $I_2$, $I_3$ and $I_4$ are measured and therefore known. These intensities may be input into the following fractions:

$$F1 = \left(\frac{I_1 - I_2}{I_1 + I_2}\right) \tag{8}$$

$$F2 = \left(\frac{I_4 - I_3}{I_4 + I_3}\right) \tag{9}$$

These are equivalent to the Fourier coefficients a and b in equations (6) and (7) above. The simple ellipsometric model is thereby given as equations (10) and (11):

$$F1 = \frac{\tan(\Psi) \times \cos(\Delta)}{1 + \tan^2(\Psi)} = \sin(2\Psi) \times \cos(\Delta) \tag{10}$$

$$F2 = \cos(2\Psi) \tag{11}$$

This is effectively equivalent to the simple reconstruction model above. However, for the complete pupil using all azimuthal angles, a different and extended model must be used. In the cases of the measured intensities $I_1$, $I_2$, $I_3$ and $I_4$, the following model may be used:

$$I_1 = C_2 S_2 (\tan^2(\Psi) + 1 - 2\tan(\Psi)\cos(\Delta)) \tag{12}$$

$$I_2 = C_4 \tan^2(\Psi) + S_4 - 2C_2 S_2 \tan(\Psi)\cos(\Delta) \tag{13}$$

$$I_3 = \tan^2(\Psi)(C_4 + C_2 S_2 + 2C_3 S_1) + (S_4 + C_2 S_2 - 2C_1 S_3) + \tan(\Psi)\cos(\Delta)(2C_1 S_3 - 2C_3 S_1) \tag{14}$$

$$I_4 = \tan^2(\Psi)(C_4 + C_2 S_2 - 2C_3 S_1) + (S_4 + C_2 S_2 + 2C_1 S_3) + \tan(\Psi)\cos(\Delta)(2C_3 S_1 - 2C_1 S_3) \tag{15}$$

where $C_n = \cos^n(A)$ and $S_n = \sin^n(A)$ and A is the azimuthal angle.

Replacing $I_1$, $I_2$, $I_3$ and $I_4$ in the fractions of equations (8) and (9) with their values in equations (12) to (15) gives rise to:

$$\frac{I_2 - I_1}{I_2 + I_1} = F1 \quad (16)$$

$$= \frac{\tan^2(\Psi)(C_4 - C_2 S_2) + S_4 - C_2 S_2 + 4\tan(\Psi)\cos(\Delta) C_2 S_2}{\tan^2(\Psi)(C_4 + C_2 S_2) + S_4 - C_2 S_2}$$

and $$\frac{I_4 - I_3}{I_4 + I_3} = F2 \quad (17)$$

$$= \frac{\tan^2(\Psi)(-4 C_3 S_1) + 4 C_1 S_3 + 4\tan(\Psi)\cos(\Delta)(C_3 S_1 - C_1 S_3)}{\tan^2(\Psi)(2 C_4 + 2 C_2 S_2) + 2 S_4 + 2 C_2 S_2}.$$

Out of the above equations (16) and (17) comes a more practical method which can be used to derive the ellipsometric results immediately from the data. Once the fractions F1 and F2 have been determined by the CCD camera, four basic functions A, B, C and D for the complete pupil including all azimuthal angles can be found:

$$A = C_4 - C_2 S_2 - C_4 \times F1 - C_2 S_2 \times F1 \quad (18)$$

$$B = S_4 - C_2 S_2 - S_4 \times F1 - C_2 S_2 \times F1 \quad (19)$$

$$C = -4 C_3 S_1 - 2 C_4 \times F2 - 2 C_2 S_2 \times F2 \quad (20)$$

$$D = 4 C_1 S_3 - 2 S_4 \times F2 - 2 C_2 S_2 \times F2 \quad (21)$$

The ellipsometric $\Psi$ can be obtained from a combination of these 4 functions and goniometric functions:

$$\tan^2(\Psi)\left(\frac{A}{C_2 S_2} - \frac{C}{C_3 S_1 - C_1 S_3}\right) = \left(\frac{D}{C_3 S_1 - C_1 S_3} - \frac{B}{C_2 S_2}\right) \quad (22)$$

After finding $\Psi$ for the whole pupil, the ellipsometric $\Delta$ can be obtained from:

$$4 \times \cos(\Delta) \times \tan(\Psi) \times \left(\frac{C_2 S_2}{A} - \frac{C_3 S_1 - C_3 S_1 - C_1 S_3}{C}\right) = \left(\frac{D}{C} - \frac{B}{A}\right) \quad (23)$$

Figure 9:
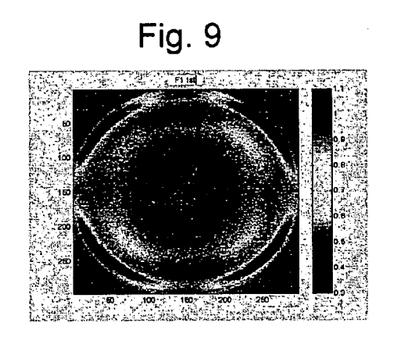
FIGS. 9 to 12 depict the resulting plots on a sensor according to an embodiment of the invention.
Figure 10:
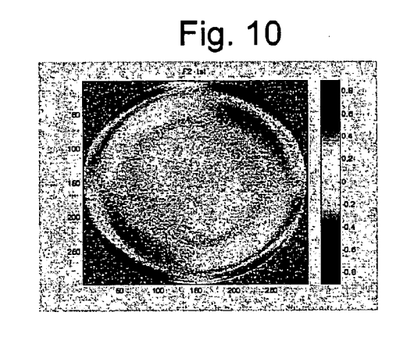
Figure 11:
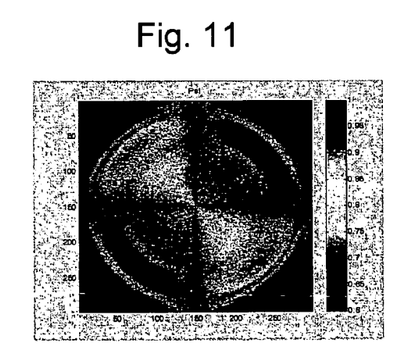
Figure 12:
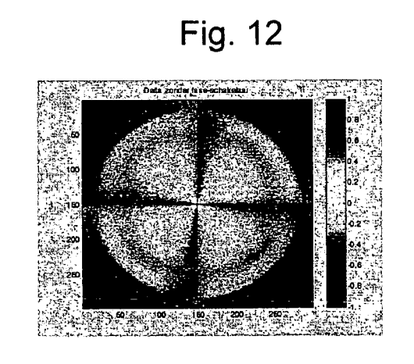

FIGS. 9 and 10 show respectively the F1 and F2 fractions of a radiation beam with a wavelength of 550 nm reflected from a D=1900 nm thick oxide resist on a silicon substrate W, with a numerical aperture of 0 to 0.92. FIG. 11 shows a resulting plot of $\Psi$ and FIG. 12 shows a resulting plot of $\cos(\Delta)$ based on the fractions F1 and F2 as shown in FIGS. 9 and 10. Both of the plots of $\Psi$ and $\Delta$ demonstrate a ring structure that is a function of radius or angle of incidence of the reflected radiation beam. The ring structure reveals the various constructive and destructive interference patterns of the radiation caused by a thick oxide layer on the surface from which the beam is reflected. Information about N, k and D or the physical parameters of the substrate can be obtained by using Fresnel equations or advanced optical models for gratings, such as RCWA and a reconstruction loop as mentioned above.

As a result of the procedure given above to obtain data from the whole pupil instead of only the diagonal, and increase of 200 times the number of available data points is usable using the same exposure time. On the other hand, the user of this method is free to use only a limited section of the pupil if desired. If, for example, only a selection of 0.2 radians out of the pupil is used, the proposed method still has 25 times more data points for $\Delta$ than the ellipsometric $\Delta$ obtained only from diagonal points according to the prior art. This gives rise to an increase of 5 times the signal to noise ratio.

Beneficially, the four pupils are measured on a dedicated CCD camera. These intensities are measured simultaneously so that no measurement time is lost. Furthermore, measuring all four outputs in parallel precludes the need for a rotating analyzer ellipsometer, which is an ellipsometer that uses a motor-driven rotating polarizer. With a rotating analyzer ellipsometer, a user has to wait for at least one revolution of the polarizer before being able to access the data for a single beam, as acquisition of the data is serial rather than parallel. The benefit of measuring all four intensities simultaneously is further that there are fewer moving components in the system. This further opens the possibility of using a pulsed radiation source such as laser. As there is no phase modulator, the scatterometer of the first embodiment is essentially independent of the wavelength used. Any errors caused by polarizing beam splitters are easily calibrated, as they are independent of the angles of incidence and of the azimuthal angles. A benefit of using Wollaston prisms (or other calcite prisms such as Glan-Thompson prisms) is that a high polarization extinction ratio is available across a large wavelength band.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An inspection apparatus comprising:
a radiation source configured to supply a radiation beam;
an optical element configured to focus the radiation beam onto a substrate;
a beam splitter system configured to split the radiation once reflected from the substrate into at least four components having different polarization orientations;
a focusing system configured to focus the four components at different positions on a detector, the detector configured to detect simultaneously angle-resolved spectra of the four components of the radiation beam;
a processor configured to use the angle-resolved spectra of the four components to determine a phase difference between polarization directions and a ratio between polarization direction amplitudes of the reflected radiation beam; and
an iterative loop device configured to determine a refractive index, an absorption index, and a thickness of a resist layer on the substrate based on a difference between the determined phase difference and a modeled phase difference and based on a difference between the determined ratio and a modeled ratio.

2. The inspection apparatus according to claim 1, wherein the beam splitter system comprises:
a beam splitter configured to separate the radiation beam once reflected from the surface of the substrate into first and second sub-beams;
a first polarizing beam splitter configured to split the first sub-beam into two respectively orthogonally polarized components; and
a second polarizing beam splitter configured to split the second sub-beam into two further respectively orthogonally polarized components.

3. The inspection apparatus according to claim 2, wherein the first and second polarizing beam splitters comprise polarizing prisms.

4. The inspection apparatus according to claim 1, wherein the processor is configured to create an image made up of arrays of pixels, a relative value (F1, F2) of each pixel having been calculated using one of the following fractions:

$$F1 = \frac{I_2 - I_1}{I_2 + I_1}, \text{ and}$$

$$F2 = \frac{I_4 - I_3}{I_4 + I_3},$$

wherein $I_1$, $I_2$, $I_3$, and $I_4$ are respective intensities of first, second, third and fourth components.

5. The inspection apparatus according to claim 1, wherein the beam splitter system comprises:

a beam splitter configured to separate the radiation beam once reflected from the surface of the substrate into first and second elliptically polarized sub-beams;
a first polarizing beam splitter configured to split the first sub-beam into first and second components with about 0 and 90 degree polarization respectively; and
a second polarizing beam splitter rotated by about 45 degrees with respect to the first polarizing beam splitter and configured to split the second sub-beam into third and fourth components with about 45 and 135 degree polarization respectively.

6. The inspection apparatus according to claim 2, wherein the first and second polarizing beam splitters comprise Wollaston prisms.

7. The inspection apparatus according to claim 1, wherein the processor is configured to determine the phase difference (Δ) between polarization directions and the ratio (tan Ψ) between the polarized radiation direction amplitudes of the reflected radiation beam from measured intensities ($I_1$, $I_2$, $I_3$, $I_4$) of first, second, third and fourth components using the following equations:

$$\frac{I_2 - I_1}{I_2 + I_1} = \sin(2\Psi) \times \cos(\Delta), \text{ and}$$

$$\frac{I_4 - I_3}{I_4 + I_3} = \cos(2\Psi).$$

8. The inspection apparatus according to claim 1, wherein the optical element is configured to focus the radiation beam onto the substrate at a range of azimuthal angles (A) from 0 to 360°.

9. The inspection apparatus according to claim 1, wherein the radiation beam focused on the substrate is elliptically polarized.

10. The inspection apparatus according to claim 1, further comprising a polarizer and a retarder to circularly polarize the radiation beam to be focused on the substrate.

11. The inspection apparatus according to claim 1, wherein the focusing system comprises an optical wedge configured to focus the components onto the detector.

12. The inspection apparatus according to claim 11, wherein the optical wedge is placed in an image plane of the focusing system.

13. The inspection apparatus according to claim 1, wherein the focusing system comprises a deflector configured to deflect the components onto the detector.

14. The inspection apparatus according to claim 1, wherein the sub-beams comprise a TE-beam and a TM-beam.

15. A method comprising:
reflecting an elliptically polarized radiation beam off a surface of a substrate;
splitting the reflected radiation beam into first and second elliptically polarized sub-beams;
splitting the first sub-beam into first and second components with polarization orientations of about 0 and 90 degrees respectively;
splitting the second sub-beam into third and fourth components with polarization orientations of about 45 and 135 degrees respectively;
focusing the first, second, third, and fourth components at different position on a detector;
simultaneously detecting the first, second, third and fourth components using the detector;
using angle-resolved spectra of the four polarization orientations to determine a phase difference between polarization directions and a ratio between polarization direction amplitudes of the reflected radiation beam; and iteratively determining a refractive index, an absorption index, and a thickness of a resist layer on the substrate using a difference between the determined phase difference and a modeled phase difference and using a difference between the determined ratio and a modeled ratio.

16. The method according to claim 15, further comprising creating an image made up of arrays of pixels, a relative value (F1, F2) of the pixels having been calculated using intensity values ($I_1$, $I_2$, $I_3$, $I_4$) of the detected radiation components at that pixel location on the detector according to one of the following fractions:

$$F1 = \frac{I_2 - I_1}{I_2 + I_1}, \text{ and}$$

$$F2 = \frac{I_4 - I_3}{I_4 + I_3}.$$

17. The method according to claim 15, further comprising determining the phase difference ($\Delta$) between the polarized radiation directions and the ratio (tan $\Psi$) between the polarized radiation direction amplitudes of the reflected radiation beam from measured intensities ($I_1$, $I_2$, $I_3$, $I_4$) of the first, second, third and fourth components using the following equations:

$$\frac{I_2 - I_1}{I_2 + I_1} = \sin(2\Psi) \times \cos(\Delta), \text{ and}$$

$$\frac{I_4 - I_3}{I_4 + I_3} = \cos(2\Psi).$$

18. The method according to claim 15, further comprising focusing the radiation beam onto the substrate at a range of azimuthal angles (A) from 0 to 360°.

19. The method according to claim 18, further comprising creating an image made up of arrays of pixels, a relative value of the pixels being associated with the ratio (tan $\Psi$) between polarization direction amplitudes of the reflected radiation beam, and the relative positions of the pixels being associated with the different azimuthal angles (A).

20. The method according to claim 18, further comprising creating an image made up of arrays of pixels, a relative value of the pixels being associated with the phase difference ($\Delta$) between the polarization direction of the reflected radiation beam, and the relative positions of the pixels being associated with the different azimuthal angles (A) of the radiation beam.

21. The method according to claim 15, wherein the splitting of the second sub-beam is carried out using a beam splitter rotated by about 45 degrees with respect to a beam splitter used for splitting the first sub-beam.

22. A lithographic apparatus comprising:
a radiation source configured to supply a radiation beam;
an optical element configured to focus the radiation beam onto a substrate;
a beam splitter configured to split the radiation beam once reflected from the substrate into at least four components having different polarization orientations;
a focusing system configured to focus the four components at different positions on a detector, the detector configured to detect simultaneously angle-resolved spectra of the four components of the radiation beam;
a processor configured to use the angle-resolved spectra of the four components to determine a phase difference between the polarized radiation directions and a ratio between polarization direction amplitudes of the reflected radiation beam; and
an iterative loop device configured to determine a refractive index, an absorption index, and a thickness of a resist layer on the substrate based on a difference between the determined phase difference and a modeled phase difference and based on a difference between the determined ratio and a modeled ratio.

23. A lithographic cell comprising:
a radiation source configured to supply a radiation beam;
an optical element configured to focus the radiation beam onto a substrate;
a beam splitter configured to split the radiation beam once reflected from the substrate into at least four components having different polarization orientations;
a focusing system configured to focus the four components at different positions on a detector, the detector configured to detect simultaneously angle-resolved spectra of the four components of the radiation beam;
a processor configured to determine a phase difference between the polarized radiation directions and a ratio between polarization direction amplitudes of the reflected radiation beam; and
an iterative loop device configured to determine a refractive index, an absorption index, and a thickness of a resist layer on the substrate based on a difference between the determined phase difference and a modeled phase difference and based on a difference between the determined ratio and a modeled ratio.

* * * * *